United States Patent
Meehan et al.

(10) Patent No.: US 7,193,719 B2
(45) Date of Patent: Mar. 20, 2007

(54) DEVICE AND METHOD FOR TUNING AN SPR DEVICE

(75) Inventors: Kathleen Meehan, Blacksburg, VA (US); Raymond E. Dessy, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 192 days.

(21) Appl. No.: 11/131,928

(22) Filed: May 17, 2005

(65) Prior Publication Data

US 2005/0270538 A1 Dec. 8, 2005

Related U.S. Application Data

(60) Provisional application No. 60/571,531, filed on May 17, 2004.

(51) Int. Cl.
*G01N 21/55* (2006.01)
(52) U.S. Cl. ..................................................... 356/445
(58) Field of Classification Search ................ 356/445, 356/369
See application file for complete search history.

(56) References Cited

U.S. PATENT DOCUMENTS

| | | | |
|---|---|---|---|
| 3,968,376 A | 7/1976 | Pierce et al. | |
| 4,889,427 A * | 12/1989 | Van Veen et al. | 356/445 |
| 5,451,980 A | 9/1995 | Simon et al. | |
| 5,986,808 A * | 11/1999 | Wang | 359/585 |
| 6,618,027 B2 * | 9/2003 | Takatori | 345/32 |
| 6,646,782 B1 * | 11/2003 | Russell et al. | 359/322 |
| 6,667,807 B2 * | 12/2003 | Lieberman | 356/445 |

OTHER PUBLICATIONS

Newsletter Modeling the Injection of Spin-Polarized Electrons into a Semiconductor.*
Berger, Charles E.H., et al., "Resolution in surface plasmon microscopy," Review of Scientific Instruments, vol. 65, No. 9, Sep. 1994, pp. 2829-2836.
Wang, S., et al., "Surface plasmon resonance enhanced optical absorption spectroscopy for studying molecular adsorbates," Review of Scientific Instruments, vol. 72, No. 7, Jul. 2001, pp. 3055-3060.

* cited by examiner

*Primary Examiner*—Gregory J. Toatley, Jr.
*Assistant Examiner*—Isiaka O. Akanbi
(74) *Attorney, Agent, or Firm*—Houston Eliseeva LLP

(57) ABSTRACT

The invention related to devices and methods wherein the conditions, under which surface plasmon resonance is established, are modified by altering the balance between orientations of the spins of charge carriers in an SPR layer. The embodiments of this invention may be used as logical gates, optical filters and absorbers, optoelectronic mixers, and tunable surface plasmon sensors.

11 Claims, 4 Drawing Sheets

DEVICE AND METHOD FOR TUNING AN SPR DEVICE

CROSS-REFERENCE TO RELATED APPLICATIONS

This application claims the benefit of an earlier filing date under 35 USC 119(e) to a U.S. Provisional Patent Application Ser. No. 60/571,531, filed on May 17, 2004, which is incorporated herein by reference in its entirety.

BACKGROUND OF THE INVENTION

This invention is related to tunable surface plasmon resonance (SPR) sensors and devices and methods utilizing the phenomenon of tunable surface plasmon resonance.

The surface plasmon waves, being oscillations of free electrons in a metallic or semiconductor film or layer, may be induced through interaction of photons with the free electrons in the film or layer. A maximum transfer of energy from the photon flux to the surface plasmon wave is observed as a decrease in the optical reflectivity of the metal or semiconductor film or layer, which occurs over a narrow set of wavelengths. This phenomenon is known as the surface plasmon resonance (SPR). The layer or film of metal or semiconductor in which SPR may be established may be referred to as SPR layer or SPR film.

The conditions required for photon-induced SPR include the requirement that the photons' electric field is aligned with the electric field associated with electron oscillations; that photon momentum is matched with that of the surface plasmons; and that the real component of the dielectric constant of the SPR layer is negative while the dielectric constants of the cladding materials on both sides of the SPR layer are positive. Thus, the photon-electron interactions are dictated by the properties of the materials used and by the wavelength, polarization, and angle of the incident light.

SPR may be observed, for example, by placing a thin layer of metal between two dielectrics with different dielectric constants, for example, glass and air. When the angle between the direction orthogonal to the glass surface and the direction of an incident p-polarized electromagnetic wave in the glass is greater than a critical angle, a total internal reflection takes place, i.e. the electromagnetic wave is fully reflected back into the glass. However, for some wavelengths and angles of incidence, the incident photons, instead of being reflected, are absorbed by plasmons in the metal; in other words, the energy of the electromagnetic wave is transferred to the plasmons. At these angles and wavelengths, the surface plasmons induced at the metal/air interface reinforce the surface plasmons at the glass/metal interface. These angles and wavelengths depend on the dielectric constant and thickness of the metal layer and on the dielectric constants of the dielectrics on the both sides of the metal.

The oscillating wave of electrons propagates along the SPR interface until it either radiatively or non-radiatively decays. Plasmon-photon interactions may be used to modulate light in a linear or a nonlinear manner. Small applied electrical fields also influence the propagation of a surface plasmon wave. Other methods of establishing surface plasmon resonance in a layer of material are known in the pertinent art.

One use of this phenomenon is observing changes in the medium on one side of the metal layer. For example, when on the air side of the metal layer a layer of some substance (with a dielectric constant different from the dielectric constant of air) begins to grow, the amount of reflected light in the glass changes because the dielectric constant of a dielectric in contact with the metal has changed.

One of the techniques used to electronically tune the surface plasmon wavelength is to apply a voltage across the metal film to change the electron density in the film. That technique has limitation in that the maximum frequency at which the voltage can be adjusted is determined by the RC time constant of the metal film. Therefore, because the area of the metal film in most SPR sensors is large, the maximum frequency tends to be low. Another technique of using various electro-optical materials for tuning imposes a restriction of the range of wavelengths that can be used in such sensor.

SUMMARY OF THE INVENTION

The present invention is a new device structure in which the injection of spin polarized electrons or holes is used to modify the dielectric constant of one or more of the materials in a sensor that also utilizes the excitation of a surface plasmon wave. The wavelength of the surface plasmon resonance is modified by the injection of the spin polarized electrons, allowing one to tune the SPR signal over the desired spectral region. The ability to tune the SPR wavelength, in turn, allows one to fabricate a number of active plasmonic device structures, such as surface plasmon resonance detection systems, with spin polarized carriers for optical computing, biological and chemical sensing applications. The performance of such structures is electronically altered through the injection of spin polarized electrons, which modifies the plasmonic structure after fabrication. Also contemplated by the present invention is the use of the electronically tunable SPR to provide a single element SPR sensor for multiple analyte detection with the increased sensitivity and measuring accuracy of a single analyte SPR sensor.

The SPR frequency for a given angle of incident photons is a strong function of the dielectric constant of the SPR layer (e.g., silver), therefore, modifications to the dielectric constant of the SPR layer cause a spectral shift in the SPR signal and a change in its amplitude.

The dielectric constant of the metal or semiconductor (which is generally a complex number) may be changed by altering the ratio of spin-up electrons to spin-down electrons in the SPR layer (for example, Ag) through the injection of spin-polarized electrons. This may be accomplished, for example, by using a spin valve, where spin-polarized electrons are injected from a ferromagnetic conductive oxide (ZnO:Mn) into the SPR layer. Another way of altering the ratio of spin-up electrons to spin-down electrons is through optical generation. Generally, such devices will be referred to as generators of spin-polarized electrons.

One embodiment of this invention is a device comprising an SPR layer capable of establishing SPR, a generator of spin-polarized electrons coupled to the SPR layer, comprising a generator control input controlling generation of spin-polarized electrons, a source of electromagnetic waves capable of inducing SPR in the SPR layer, and a detector of electromagnetic waves capable of detecting electromagnetic waves reflected by the SPR layer.

In this device, the generator may be an electronic injector of spin-polarized electrons or an optical generator; the SPR layer may be metal or semiconductor.

Another embodiment may further comprise a source control input coupled to the source, the source control input being a logic gate input, and a detector output coupled to the detector, the detector output input being a logic gate output, wherein the generator control input is another logic gate input.

In another embodiment, the source produces electromagnetic waves with multiple wavelengths, and the generator control input selects the wavelengths of electromagnetic waves absorbed by the SPR layer.

The electromagnetic waves absorbed by the SPR layer may pass through the SPR layer and exit it.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE SEVERAL VIEWS OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE INVENTION

The injection of spin polarized electrons at the dielectric/metal interface changes the ration of the spin-up to spin-down electrons without creating excess charge and without affecting the total concentration of electrons. The injection, however, alters the dielectric constant of the metal or semiconductor due to the change in the concentration of the spin-up electrons in the metal/semiconductor layer. The change of the dielectric constant, in turn, changes the wavelength at which SPR occurs.

Described below is a representative set of embodiments of the present invention, which will permit the electronic injection of spin polarized electrons. Other structures of varying complexity can be fabricated based on the principles of injection of spin polarized electrons, which structures can be further integrated with other electronic or optical structures to implement devices for optical computing and sensing as described below. For example, the active SPR devices can be integrated into logic gates and memory gates in optical computing architecture.

Figure 1:
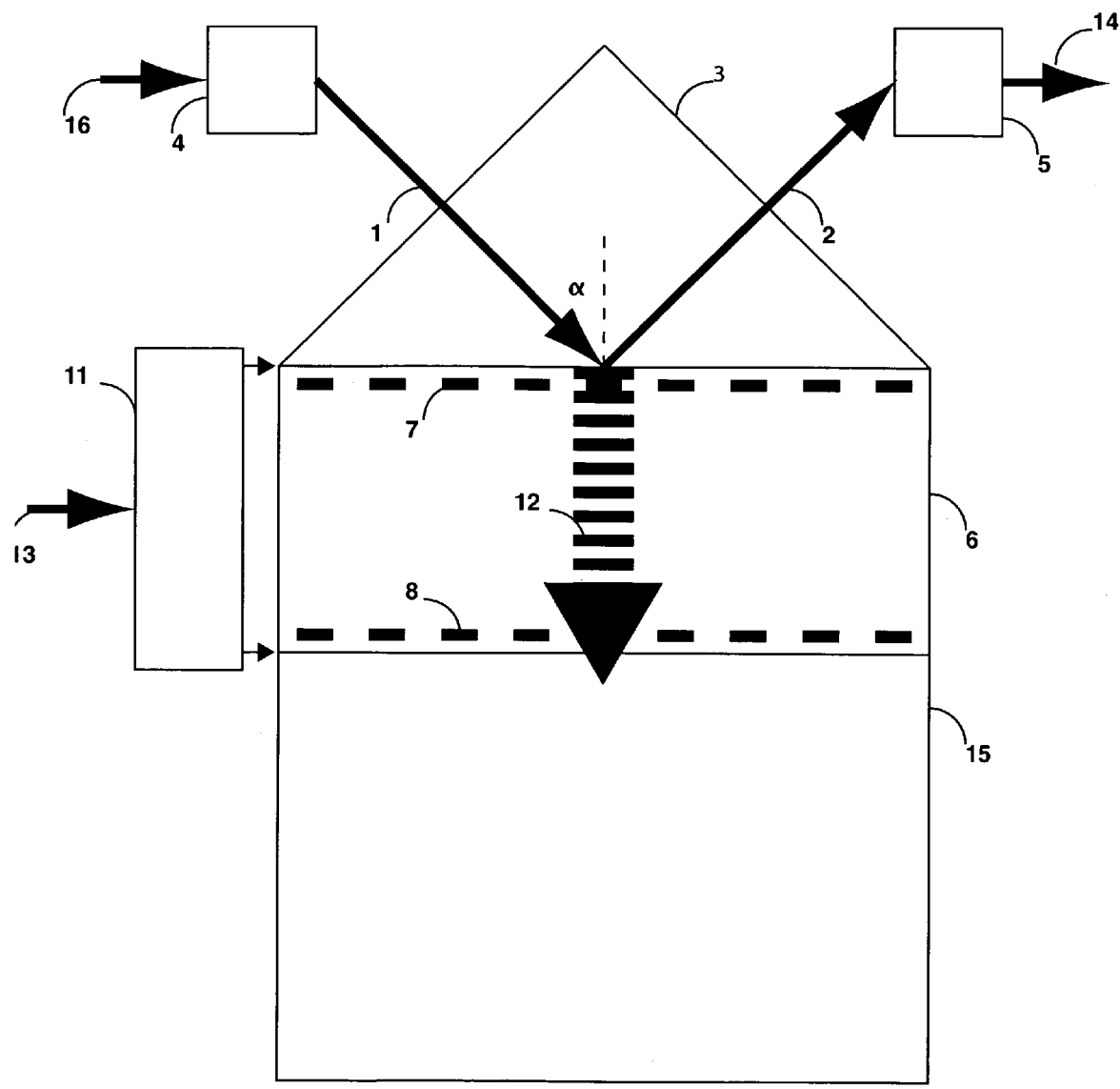
FIG. 1 schematic illustration of a spin polarized injected SPR structure.

As shown in FIG. 1, a p-polarized electromagnetic wave 1 from the source 4 passes through a prism 3, made, for example, of glass, at an angle α to the surface of dielectric 15, for example, air. In this embodiment, the prism serves as the energy conductor delivering energy into the SPR layer 6, which, for example may be a metal film on the surface of the prism 3.

The photons of the electromagnetic wave 1 may be reflected off the surface 6 and be detected by the detector 5. These photons may also be absorbed by the layer 6 and their energy 12 be used for establishing resonance of surface plasmons on the metal-glass interface 7 and surface plasmons on the metal-air interface 8.

The amount of reflected energy is measured by the detector 5.

The generator of spin-polarized charge carriers 11 alters the balance between spin orientation of charge carriers within the metal 6, which in turn changes the dielectric constant of the metal and the wavelength at which the electromagnetic wave 1 causes the surface plasmon resonance to be established. This alteration of balance may occur at high frequency as no net charge is moved by this process.

The device shown in FIG. 1 may function as a mixed input AND gate, in which input 16 controls the source of electromagnetic waves 4, input 13 controls the generator 11, and the reflected photon signal 2 is the output. The photon signal 2 is reflected only when the input 16 (which may be electronic) shifts the wavelength of the SPR away from the wavelength of the photonic input signal 1. Mixed input OR, NAND, and NOR gates are contemplated through similar electronic tuning of the SPR signal.

The surface plasmon waves can be manipulated using plasmonic optics in a similar manner to that of light waves using geometric optics. Mirrors, lenses, beam splitters and other optical elements, such as Y couplers, are possible. Extremely short lifetimes for the surface plasmon waves (or surface plasmon polaritons) have been measured—10 fs to 800 fs have been measured in Au and Ag films and Ag nanoparticles. Thus, extremely short switching speeds for the plasmonic devices are anticipated. Surface plasmon waves have been observed to propagation for relatively long distances, 100's of microns, before they decay either radiatively or nonradiatively when fabricated on electrically insulating substrates. Distances greater than 1 cm are possible through proper selection of the physical and optical properties of the metal and the dielectrics cladding the metal. As surface plasmons can easily be excited in single nanoparticles, arrays of these nanoparticles can form the active region in a plasmon waveguide structure. When illuminated in the near field of a fiber optic or semiconductor laser diode, the plasmonic devices overcome the diffraction limit constraint usually placed on all-optical devices. In addition, the spatial distribution of the surface plasmon wave perpendicular to the direction of its propagation is determined by the dimensions of the metal nanoparticles and is independent of the mode shape and wavelength of the photon that generated the surface plasmon wave. Therefore, the interaction of the local electromagnetic field of the photon with the plasmons means that the plasmonic devices can have extremely small cross-sectional areas, well under 500 nm$^2$. Similarly, shorter length devices are required to implement certain logical functions for plasmonic gates than for the equivalent photonic gate. Therefore, plasmonic logic structures are physically orders of magnitude smaller than the equivalent photonic logic gates in all three dimensions.

The surface plasmon waves can be optically excited and electrically excited. They can be modulated electrically either directly or indirectly through electronic modification of the optical properties of the dielectric material surrounding the metal. Not only will they decay nonradiatively, the nanoparticles can emit light via a radiative decay process. Furthermore, they can electrically couple to a neighboring metallic structure to excite a second surface plasmon wave. Given the modes through which the surface plasmon wave may be excited, modulated, and decay, there is considerably more flexibility in the design of a plasmonic logical gate than there is in the design of a photonic gate. Hence, the design of plasmonic logical gates with optical inputs and outputs is possible as are other input/output configurations for mixed signal computing.

The device shown in FIG. 1 may also function as a notch absorber, where the input 13 controls which wavelength are absorbed by the metal 6. The notch absorber may be used in random access-style optical memory circuits and readout circuitry. For example, the memory elements composed of similar three-layer structures absorb certain sets of wavelengths based upon the spectral position of the SPR. The device absorbs certain sets of wavelengths based upon the spectral position of the SPR, which is shifted based upon the setting of the generator 11.

The device shown in FIG. 1 may also function as a bandpass filter, in which the set of wave length cross-coupled across the metal layer 6 (through the process of radiative decay of the induced surface plasmon wave) is electronically tuned. This arrangement may be used in optical memory circuits and readout circuitry.

The device shown in FIG. 1 may also function as an optoelectronic mixer based on the phenomenon that the surface plasmon wave induced by a photon can radiatively decay. The wavelength of the re-emitted photons 2 may be adjusted through the electronic interactions between the induced surface plasmon wave 7 and 8 and the injected electrons traveling through the metal layer 6 from the generator 11. The direction of current flow from the generator 11 modifies the velocity of the surface plasmon wave thus changing the wavelength of the photons 2 emitted when the wave decays. This arrangement may be used as a logic gate, where the function table is based upon spectral shifts rather than optical intensities. This arrangement also may be used as a tunable second harmonic generator, which also may be used in optical logic gates.

The device shown in FIG. 1 may function as a tunable plasmon sensor detecting changes in the dielectric constant of the dielectric 15. One of the applications of such electronically tunable SPR sensor is in high throughput biosensor systems—SPR biosensors, in which binding of the molecules to a specially designed layer at the metal surface results in a shift of the resonance angle of the SPR sensor. The electronic tuning of the sensor is made by adjusting the ratio of spin-up and spin-down electrons in the SPR layer 6 by adjusting the settings of the generator 11. The described tunable SPR sensor has the ability to serve as a single sensor detecting multiple analytes, dramatically increasing the throughput of such sensor system.

Figure 2:
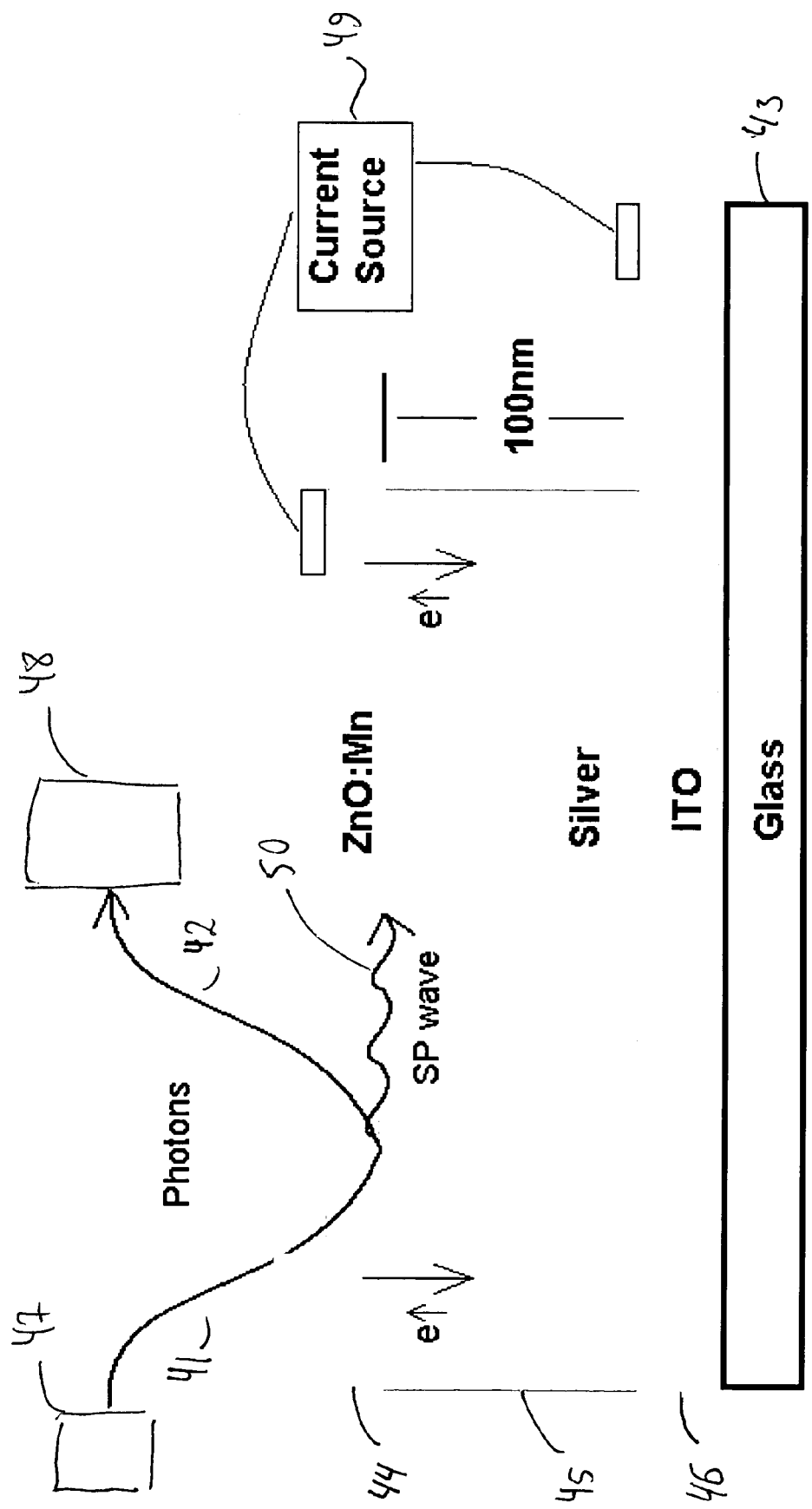
FIG. 2 is a schematic illustration of a modified spin valve SPR structure with electron injection perpendicular to the surface plasmon interface.

FIG. 2 shows an embodiment of this invention integrating a modified spin valve structure with a standard SPR structure to allow tuning of the wavelength and amplitude of SPR phenomenon through controlled injection of spin-polarized electrons into the SPR structure. The three layer structure deposited on a glass slide 43 is composed of a transparent conductive ferromagnetic oxide 44 (Mn-doped ZnO), a thin layer of silver (~100 nm) 45, and an Iridium-Tin-Oxide layer 46. The silver layer, which serves as the SPR layer is e-beam evaporated on top of the coated substrate followed by the deposition of Mn-doped ZnO. Al contact pads are deposited and patterned on the oxides to facilitate the connection of the power supply leads.

Figure 3:
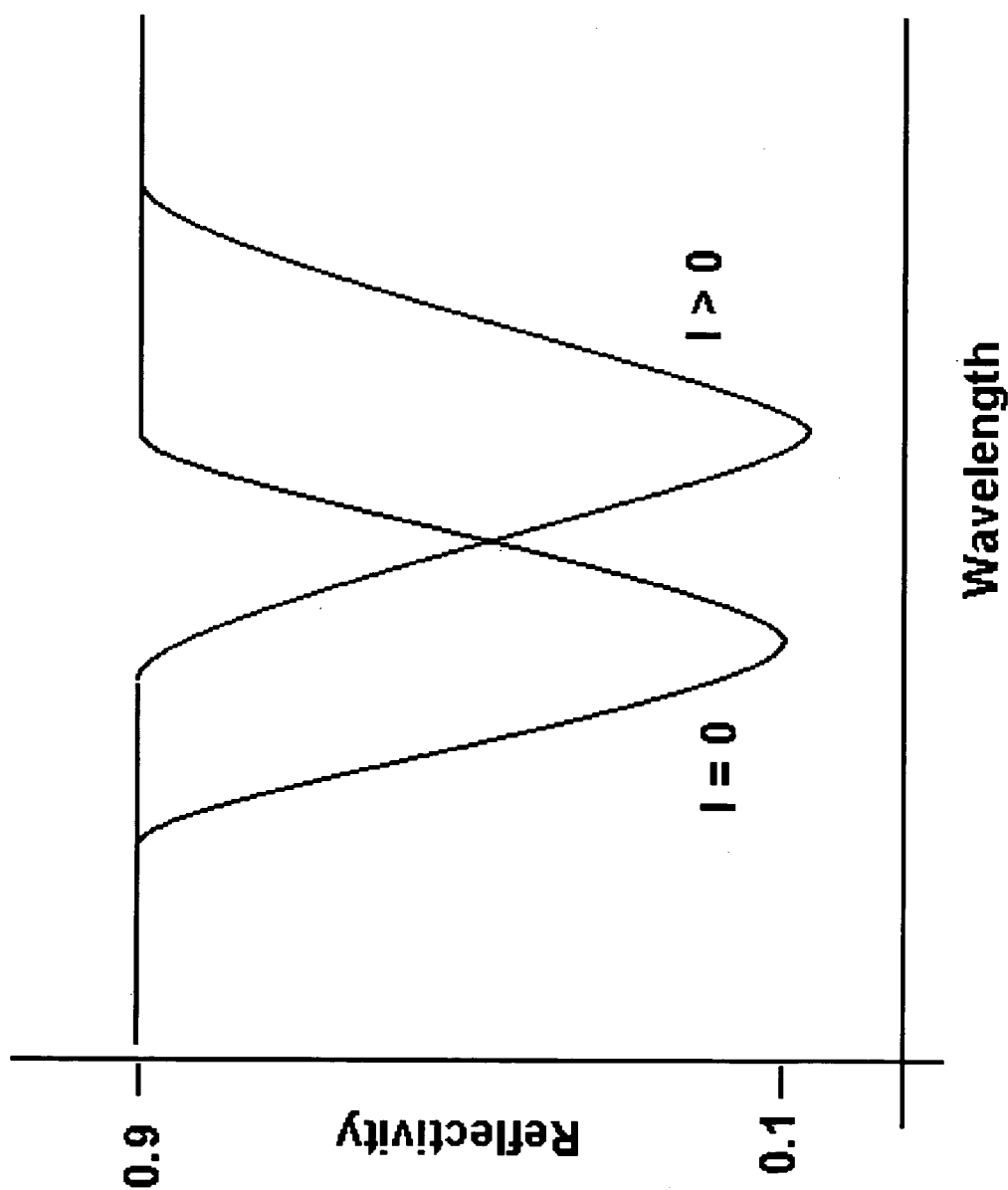
FIG. 3 shows dependence of reflectivity on wavelength for different values of spin-polarized current.

Following fabrication, the magnetic dipoles in the ferromagnetic oxide are aligned by placing the structure in a high magnetic field. After the magnetic dipoles are aligned, optical characterization of the structure may be performed without the presence of a magnetic field. The illumination source 47 is a tungsten halogen source, the output 41 of which is filtered so that only p-polarized photons illuminate the structure at a fixed angle of incidence. Reflected light 42 is collected and directed into a spectrometer 48, which spectrally disperses the light. The intensity of the light is detected using a photomultiplier tube. The relationship of reflectivity versus wavelength as functions of injected spin-polarized current I from the source or generator 49 is shown in FIG. 3.

The diffusion length of the spin-polarized electrons in silver is long, about several microns, before scattering randomizes the electrons' spin. Given that the path length of the electrons in silver is 100 nm, there is minimal spin randomization as the electrons move through the thin layer of Ag. Therefore, the current driven through the silver film 45 is proportional to the concentration of excess spin-up electrons in the silver 45. In this embodiment, the bias voltage used to drive the current through the silver film 45 is perpendicular to the electric field induced by the energy transfer from the photons 41 to the surface plasmon wave 50 in the silver film 45. No component of the electric field of the surface plasmon wave 50 is in the same plane as the electric field associated with the applied bias.

Figure 4:
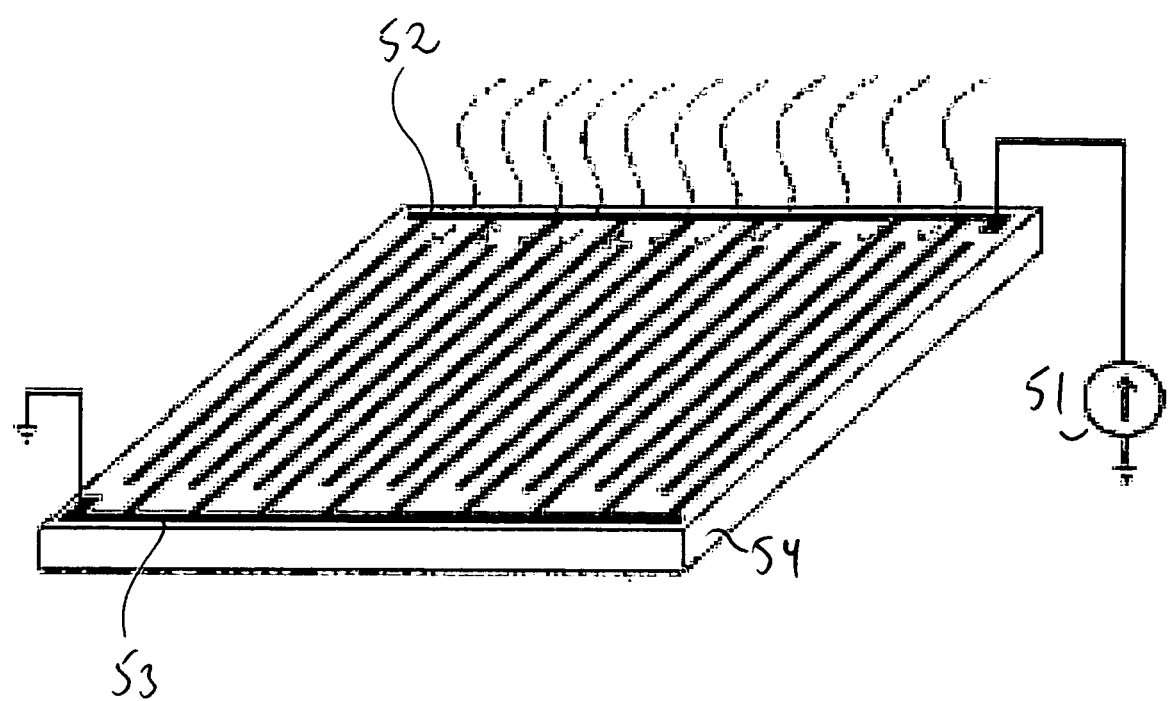
FIG. 4 shows an embodiment where the current is injected in parallel with surface plasmon waves.

FIG. 4 shows an arrangement of electrodes for spin-polarized electron injection where the electron current from the generator 51 passes through the SPR layer 54 between the electrodes 52 and 53 in parallel with the direction of surface plasmon waves. Because of the interaction between the current and the surface plasmons, this arrangement allows changing the frequency of the photons reemitted by the SPR layer by altering the current from the generator 51.

Those devices, circuits and other embodiments of the present invention can be used to modulate the intensity and spectral content of the photons incident upon them. Miniaturization of the aforementioned embodiments of this invention may be achieved through nanotechnology, for example by the growth of core-shell nanoparticles, deposition of multilayer nanowire structures in alumina nanopores, and by other methods.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A device comprising:
    an SPR layer capable of establishing surface plasmon resonance,
    a generator of spin-polarized electrons coupled to the SPR layer, comprising
        a generator control input controlling generation of spin-polarized SPR electrons,
    a source of electromagnetic waves capable of exciting the surface plasmon resonance in the SPR layer, and
    a detector of electromagnetic waves capable of detecting electromagnetic waves reflected by the SPR layer.

2. The device of claim 1, wherein the SPR layer is metal.

3. The device of claim 1, wherein the SPR layer is semiconductor.

4. The device of claim 1, wherein the generator is an electronic injector of spin-polarized electrons.

5. The device of claim 1, wherein the generator is an optical generator.

6. The device of claim 1, further comprising
a source control input coupled to the source, the source control input being a logic gate input, and
a detector output coupled to the detector, the detector output input being a logic gate output,
wherein the generator control input is another logic gate input.

7. The device of claim 1, wherein
the source produces electromagnetic waves with multiple wavelengths, and
the generator control input selects the wavelengths of electromagnetic waves absorbed by the SPR layer.

8. The device of claim 7, wherein the electromagnetic waves absorbed by the metal layer are passing through the metal layer and exiting it.

9. The device of claim 1, wherein
the generator control input selects the difference between the wavelength of electromagnetic waves re-emitted by the SPR layer.

10. The device of claim 1, wherein
the change in the detector output is indicative of change in dielectric properties of a medium adjoining the SPR layer.

11. A method of electronically tuning an SPR device by altering the wavelength and/or direction of electromagnetic waves required to excite a surface plasmon resonance wave in an SPR layer, the method comprising altering the balance between electrons having different spin orientations in the SPR layer.

* * * * *